United States Patent [19]

Ehrenkranz

[11] Patent Number: 4,769,215
[45] Date of Patent: Sep. 6, 1988

[54] INTEGRITY PRESERVING AND DETERMINING URINE SAMPLE COLLECTION APPARATUS

[75] Inventor: Joel R. L. Ehrenkranz, New Vernon, N.J.

[73] Assignee: Franklin Diagnostics, Inc., Morristown, N.J.

[21] Appl. No.: 29,727

[22] Filed: Mar. 24, 1987

[51] Int. Cl.$^4$ .................. B01L 3/00; G01N 1/10; G01N 21/77
[52] U.S. Cl. .................. 422/58; 73/863.52; 128/771; 422/102
[58] Field of Search .................. 128/761, 771; 73/863.52; 422/61, 102, 68, 58; 374/157, 159

[56] References Cited

U.S. PATENT DOCUMENTS

| | | | |
|---|---|---|---|
| 3,351,050 | 11/1967 | Naftolin | 128/761 |
| 3,568,218 | 3/1971 | Beckman . | |
| 3,586,041 | 6/1971 | Monestere . | |
| 3,811,136 | 5/1974 | Whitney et al. | 128/761 X |
| 3,928,875 | 12/1975 | Parson . | |
| 4,059,124 | 11/1977 | Hill . | |
| 4,064,760 | 12/1977 | Benjamin . | |
| 4,211,749 | 7/1980 | Kastner . | |
| 4,221,295 | 9/1980 | Tuchband et al. . | |
| 4,241,017 | 12/1980 | Balistreri et al. | 422/102 X |
| 4,396,113 | 8/1983 | Gail et al. . | |
| 4,443,896 | 4/1984 | Porat et al. . | |
| 4,457,314 | 7/1984 | Knowles . | |
| 4,466,445 | 8/1984 | Abrams . | |
| 4,492,258 | 1/1985 | Lichtenstein et al. | 422/102 X |
| 4,494,581 | 1/1985 | Gordon . | |
| 4,564,299 | 1/1986 | Ehrenkranz . | |
| 4,569,090 | 2/1986 | Muller . | |

FOREIGN PATENT DOCUMENTS 8000406  3/1980  PCT Int'l Appl. .................. 422/102

Primary Examiner—Barry S. Richman
Assistant Examiner—Robert J. Hill, Jr.
Attorney, Agent, or Firm—Richard C. Woodbridge

[57] ABSTRACT

A urine collection apparatus includes a tamper-proof, one way valve to make sure that freshly voided samples of urine are not tampered with. A chemical type thermometer is located in the reservoir to make sure that the urine sample is fresh when collected. An enzyme poison detector station helps to insure that bleach or other chemicals haven't been added to the urine to adulterate the specimen. The one way valve preferably comprises a trap door that closes as the urine sample fills up the reservoir. The presence of an adhesive substance around the edge of the trap door keeps the trap door shut after the urine sample has been collected.

11 Claims, 3 Drawing Sheets

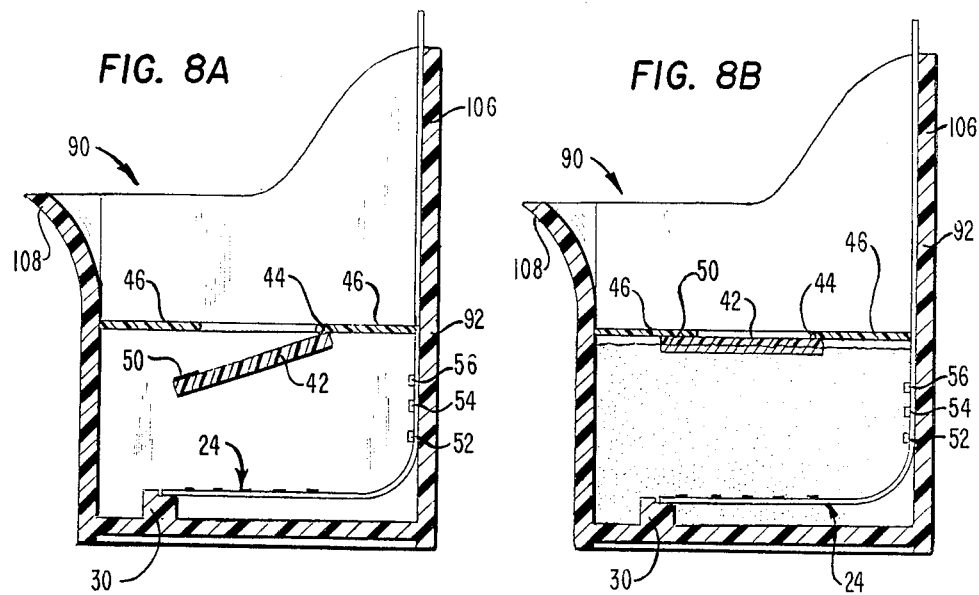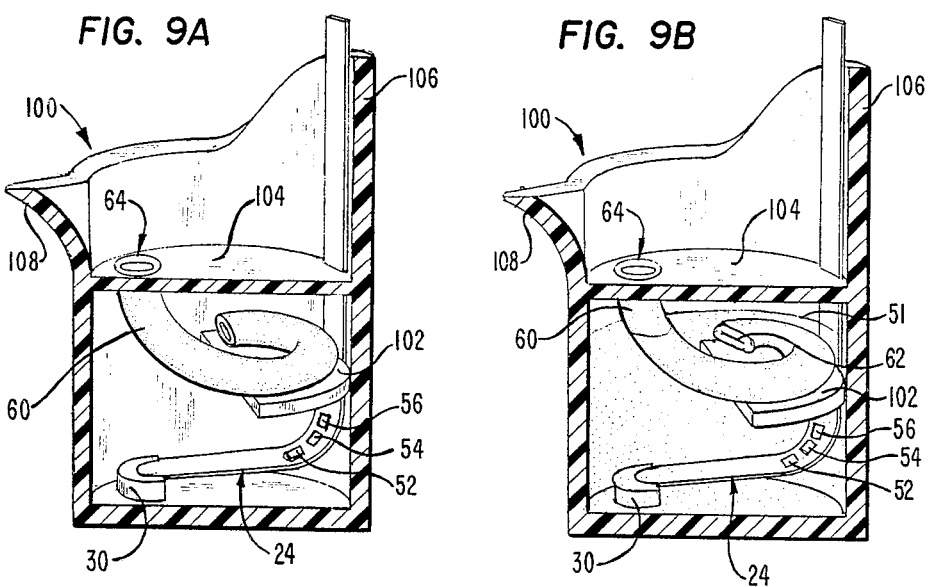

INTEGRITY PRESERVING AND DETERMINING URINE SAMPLE COLLECTION APPARATUS

BACKGROUND OF THE INVENTION

1. Field of the Invention

This invention relates to an apparatus for determining if a urine specimen is fresh and unadulterated and for preventing tampering with the urine specimen after it has been collected.

2. Description of Related Art

Over the last few years there has been a significant rise in accidents related to possible drug use. Many of the accidents occur in manufacturing plants, however, drugs are becoming more and more implicated in automobile, airplane and railroad accidents. As a consequence, there has been renewed interest in the testing for the presence of drugs in the workplace. However, there are two major problems. First, it has been felt necessary to monitor the taking of urine samples to guarantee the integrity of the test results. Second, the testing aspect, especially coupled with monitoring, has raised concerns about possible invasion of privacy. Accordingly, a need is recognized for a urine sample collector that can minimize the invasion of an individual's privacy yet maximize the integrity of the sample of urine taken.

A general review of the prior art discloses a number of urine collectors, but none that appear to be concerned with the joint problems of privacy and integrity associated with drug testing.

The prior art does disclose some literature describing urine measuring devices incorporating a temperature sensor therein. Perhaps most relevant of that group is U.S. Pat. No. 4,564,299 entitled BODY LIQUID TEMPERATURE MEASURING DEVICE issued to Joel R. L. Ehrenkranz who is also the inventor of the device described in specification of this disclosure. A chemical melting point thermometer is located in the bottom of the urine collecting receptacle. The primary purpose of the invention is to determine when a human female is close to ovulation. Because of the nature of the thermometer therein, it is possible to determine if the sample of urine was warm or cold when received, thereby determining if the sample was a freshly voided sample.

The patent literature also describes devices, in other context, which employ valve-like devices in urine collecting embodiments. The primary purpose of those valves is to prevent spillage after the urine is collected and prior to its being destroyed. For example, U.S. Pat. Nos. 3,356,218 and 4,457,314 disclose valve-like devices in two different types of urine collectors. The valve in U.S. Pat. No. 4,457,314 is described as an "anti-back flow mechanism" employed primarily to prevent spillage of the contents. Other U.S. Patents that disclose one way type of valves for the purpose of preventing spillage include: U.S. Pat. Nos. 3,928,875; 4,095,124; 4,586,041 and 4,734,154.

Another class of valve urine collectors involve those designed to collect mid-stream urine samples. For example, U.S. Pat. No. 4,494,581 discloses a mid-stream urine collection device which describes, in FIG. 7 thereof, a mechanism in which a floating cork closes a valve after an initial sample of urine has been obtained so that the remaining specimen to be collected will be from the mid-stream. Other possible relevant mid-stream urine collection devices include those described in the following U.S. Pat. Nos. 4,064,760; 4,221,295 and 4,569,090.

Lastly, the following U.S. Patents are cited as being of only general possible relevance: U.S. Pat. Nos. 3,396,113; 4,211,749; 4,443,896 and 4,466,445.

Insofar as understood, none of the prior art addresses the problems inherent in a drug testing program where the drug sample has to be virtually tamper-proof yet the individual's right of privacy has to be observed.

SUMMARY OF THE INVENTION

Briefly described, the invention comprises a urine collection device specifically appropriate for use in drug screening programs. A urine receiving reservoir includes a chemical type thermometer located near the bottom thereof for documenting the freshness of the urine sample immediately after voiding. Urine enters the reservoir through a one-way valve that substantially prevents an individual from filling the reservoir with fresh urine, thereby setting the temperature sensor, and then subsequently emptying the first fresh sample and substituting it with a second nonfresh sample that might be free of drug contaminants. The one way valve includes tamper-proof features such as a twisted path or a urine activatable adhesive that makes it virtually impossible to remove the original sample once its collected in the reservoir. The reservoir also includes chemical reagent stations to further discourage or detect tampering or adulteration. One reagent station can determine if the urine sample has been watered down by detecting the specific gravity of the sample. A second reagent station measures the pH of the urine. A third station includes a chemical reagent that helps determine if an enzyme poison, like bleach, has been added to the urine sample in order to disguise the presence of drugs such as cannabis, cocaine, opiates, amphetamines, sedatives and hallucinogenics. Because the urine collector is virtually tamper-proof, it eliminates or greatly reduces the need to have the voiding procedure humanly monitored by another individual. This in turn increases the individuals privacy while also guaranteeing that the employer has a fresh, unadulterated, high integrity urine sample.

According to an alternative embodiment of the invention, the one way valve includes a specific gravity sensitive mechanism which only passes urine specimens into the collector if the urine specimen is within the correct range of acceptable specific gravity levels. In other words, if a sample of urine is adulterated with water, the reservoir will not accept the urine sample.

Lastly, another embodiment is described having the same basic structure of the preferred embodiment, but housed in a receptacle more familiar to human males.

These and other features of the invention will be more fully understood by reference with the following drawings.

BRIEF DESCRIPTION OF THE DRAWINGS

FIG. 8A is an alternative embodiment of the invention in a form more familiar to males and shown in the state before the receptacle is filled with urine.

FIG. 8B illustrates the same receptacle shown in FIG. 8A except that the one way valve has been closed by the presence of the urine sample in the receptacle.

FIG. 9A illustrates an embodiment similar to that shown in FIG. 8A except that the one way valve comprises a flattened piece of rubber tubing.

FIG. 9B illustrates the embodiment of FIG. 9A with the reservoir filled and the valve closed.

DETAILED DESCRIPTION OF THE INVENTION

During the course of this description like numbers will be used to identify like elements according to the different figures which illustrate the invention.

The present invention 10 as shown in FIGS. 1-5 is an improvement over the invention described in my U.S. Pat. No. 4,564,299. Therefore, in order to better understand the invention the same element numbers are used throughout this disclosure as were used in U.S. Pat. No. 4,564,299.

Figure 1:
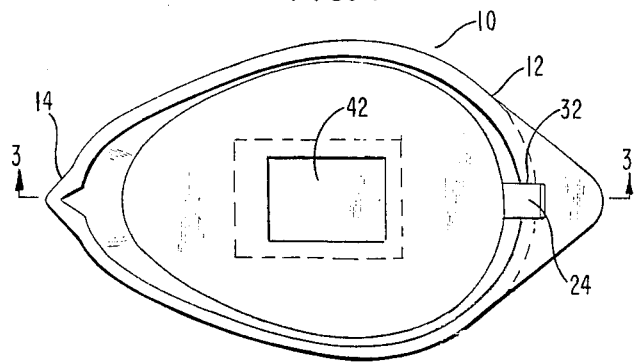
FIG. 1 is a top plan view of the receptacle according to the preferred embodiment of the invention.
Figure 2:
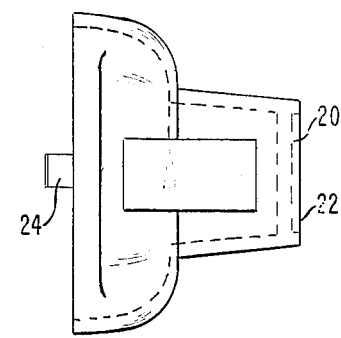
FIG. 2 is an end view of the receptacle of FIG. 1.

FIG. 1 illustrates a receptacle 10 having a generally elliptical upper portion 12 which has, at a side thereof, a pouring spout 14. The device 10, according to this preferred embodiment, is intended to provide a circumferential upper lip portion 16 suitable to receive a lid 17 which is intended to be force fitted over the lip 16 to provide an air and liquid tight closure. Lid 17 has the general configuration of upper lip 16. The device 10 further includes a base portion which functions to receive a urine sample, and also functions to stabilize the device for stacking or storage. Accordingly the upstanding walls 19 are slightly tapered. The base 18 is intended to hold a sample in the range of 60 to 150 cc of urine.

The accuracy of the invention 10 depends upon minimizing temperature variations due to surface cooling, or heat conducted from the base of the container. Accordingly, the base portion 18 is of restricted surface area as compared to the upper funnel portion 12. Most importantly, the base 18 defines a recess 20 which provides a dead air space insulating the sample contained within the device 10 from the surface upon which the base 18 rests. A circumferential edge 22 of restricted diameter is provided to support the device on a surface (not shown) during storage. Prior to use, however, units 10 can be stacked in the conventional fashion, one within another. After use the lid 17 may be affixed for storage if the sample is to be retained.

Although the device of this invention 10 is suitable for use with any temperature measurement means, the preferred embodiment includes a chemical thermometer 24 which contains a temperature array 26 mounted on a bendable plastic substrate. The term "chemical" or "chemical-type" thermometer is used in this disclosure to include and describe both melting point and liquid crystal type thermometer which are the preferred thermometer types; however, it would also be possible to use mercury or electronic thermometers as alternatives. The temperature array 26 on the substrate 28 is received on a mounting pedestal 30 and may be affixed thereto with a permanent or temporary adhesive, as desired.

The device 24 is typically bent to extend the length of the base 18 and is received along a groove 32 in the side wall 34 of the device 10. The temperature measuring device 24 may be either secured by a conventional adhesive, or force fitted into the groove 32. In either event, it is intended in the preferred embodiment 10 that the assembled device be stackable for ease in dispensing. The device 24 may be removable for storage.

The pedestal 30 is critical to the device of this invention in that it provides a depth locator for the thermometer 24 to minimize the effect of the cooling gradient at the exposed surface of the sample.

As noted above, any conventional temperature measuring device is suitable for use with the device of this invention. It is preferred, however, to use either a chemical melting point or liquid crystal type thermometer available from American Thermometer Co. or a melting-point type thermometer available from Info-Chem, Inc., Fairfield, N.J. The latter thermometer is normally not reusable, and reusable thermometers are available from American Thermometer Co. These thermometers produce an accuracy of plus or minus 0.2 degrees C. in measurement of deep body temperature using urine samples voided directly into the device 10. Similarly, the temperature reading can be used to document that the sample was fresh, thereby demonstrating sample integrity.

The structure so far described is similar to that set forth in U.S. Pat. No. 4,564,299. The major improvement comprises the inclusion of a one way valve mechanism 40 that permits the receptacle 10 to receive a first sample of urine but prevents that first sample from being discharged and replaced with a second sample.

One way valve mechanism 40 includes a trap door 42 connected by a pliable plastic hinge 44 to the upper surface 46 which in turn is rigidly attached to the side walls 19 of the base 18. The trap door 42 preferably has a buoyancy such that it will float in urine. Therefore, as the reservoir 18 fills up with urine the trap door 42 will close against the underside of upper surface 46. A urine liquid activatable adhesive 50 is located at the interface between trap door 42 and upper surface 46. The purpose of adhesive 50 is to seal the door 42 shut after it has received its urine sample 51. The liquid activatable adhesive 50 preferably comprises a double coated acrylic foam but could also comprise adhesive transfer tapes both of which are manufactured by the Minnesota Mining and Manufacturing Corporation. Also included in the base 18 are a plurality of a reagent stations 52, 54 and 56. The primary purpose of reagent stations 52, 54 and 56 is to make sure that the urine specimen has not been adulterated.

Reagent station 52 preferably comprises a specific gravity testing material. An acceptable specific gravity detecting solid phase reagent system is available from the Ames Division of Miles Laboratory, Elkhardt, Ind. The preferred reagent is: 2.8% w/w bromthymol blue; 68.8% w/w poly (methyl vinyl ether/maleic anhydride); 28.4% w/w sodium hydroxide. Reagent station 54 preferably comprises a small pH test chemical. An acceptable pH detector is also available from the Ames Division of Miles Laboratory, Elkhardt, Ind. The preferred reagent is: 0.2% w/w methyl red; 2.8% w/w bromthymol blue; 97.0% w/w nonreactive ingredients. Litmus paper may also be acceptable. Reagent station 56 preferably comprises an enzyme poison detector. The invention 10 preferable comprises all three reagent stations 52, 54 and 56 but could comprise only one or two of the reagent stations depending upon the level of integrity requires. The thermometer 24 can be permanently attached to the pedestal 36 so that it can not be removed or, alternatively, it maybe made removable for remote inspection.

Figure 3A:
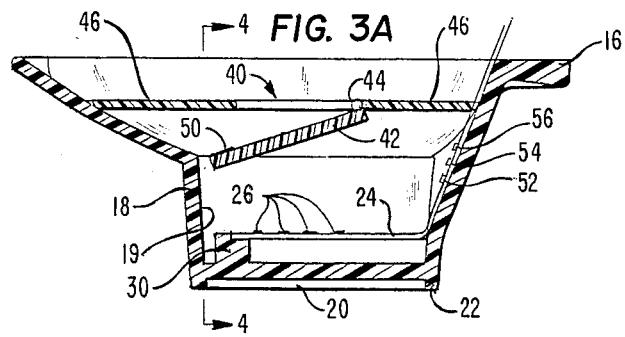
FIG. 3A is a cross-sectional view taken along lines 3—3 of FIG. 1 showing the invention before the receptacle is filled with urine.
Figure 3B:
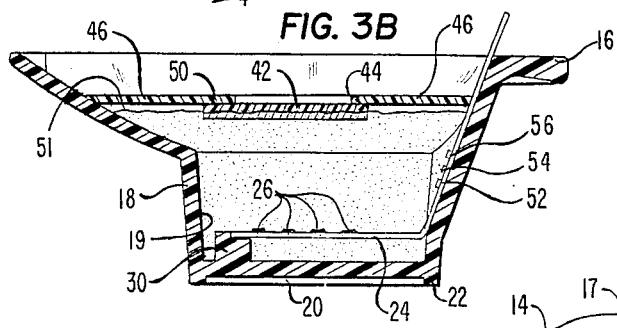
FIG. 3B is another cross-sectional view taken along lines 3—3 shown after the receptacle has been filled with urine.
Figure 4:
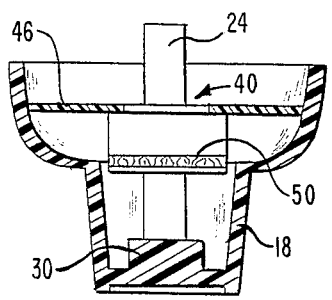
FIG. 4 is an end cross-sectional view of the receptacle of FIG. 1.
Figure 5:
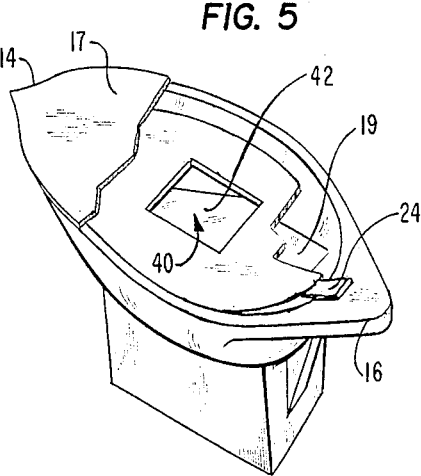
FIG. 5 is a perspective view of the invention showing the top surface thereof partially broken away.

FIG. 3A illustrates the preferred embodiment of the invention 10 with the one way valve 40 open. FIG. 3B illustrates the mode where the base 18 has filled up with urine 51 causing the trap door 42 to float upward against upper surface 46. Liquid activatable adhesive 50 seals the trap door 42 shut thereby preventing tampering.

The use of a temperature detector 24 is believed to be a fairly reliable method for determining the freshness of urine. It is also believed to be an acceptable alternative to physical observation. For a discussion of the foregoing, note the article entitled "Measurement of Urine Temperature As An Alternative to Observed Urination in a Narcotic Treatment Program", Judson, et al, AM. J. Drug Alcohol Abuse 6(2) pages 197–205 (1979) and "A New Method for Measuring Body Temperature", Joel R. L. Ehrenkranz, M.D., New Jersey Medicine, Journal of Medical Society of New Jersey, January 1986, Vol. 83, No. 2, pages 93–96. The use of a tamper proof one way valve mechanism 40 increases the integrity of the invention 10. The major advantage of a tamper proof one way valve 40 is that it prevents an individual from providing a first sample of urine at body temperature, then disposing of the first sample and replacing it with a cooler second sample of urine that may be free of drug symptoms.

Finally, the use of reagent 52, 54 and/or 56 stations further increase the integrity of the sample. Of the reagent stations 52, 54 and 56, the most important is probably the enzyme poison detector 56.

The enzyme poison detector 56 used preferably consists of glucose oxidase, peroxidase, and potassium iodide, but other enzyme systems including alkaline phosphatase, glucose-6-phosphate dehydrogenase, ATPase, proteases, DNAases, RHAases or for that matter any enzyme which when exposed to the appropriate substrate yields a color change reaction could also be employed.

To determine the reliability of the apparatus to document freshness and detect adulteration, the following three sets of experiments were performed:

In the first series of experiments, urine was voided directly into a Franklin collector and allowed to stand for 15 minutes. The Franklin Collector is a commercially available urine collector that can be obtained from Franklin Diagnostics, Inc., 60 Franklin Street, Morristown, N.J. 07960. During this 15 minute period, a previously collected urine sample contained in a standard urine collection bottle as provided by, for example, CompuChem, Inc. or Roche Diagnostics, was held either in the armpit or between the thighs of the individual who had provided the fresh specimen for a period of 15 minutes and then poured into a separate Franklin Collector and the temperature of the two collectors compared. The results are listed below:

| Experiment #1 | | | | |
|---|---|---|---|---|
| | #1 | #2 | #3 | #4 |
| fresh | 97.8 | 98.0 | 98.6 | 99.2 |
| old | <96.0 | <96.0 | <96.0 | <96.0° F. |

This experiment demonstrated that there is complete discrimination on the basis of temperature between fresh and previously collected (old) urine samples using the Franklin Collector. Other attempts at using temperature as a documentation of freshness (see p. 202 of paper cited above entitled Measurement of Urine Temperature as an Alternative to Observed Urination in a Narcotic Treatment Program) have not been able to completely discriminate fresh from old urine.

In the second set of experiments, the effects of household bleach (5.25% sodium hypochlorite), the enzyme poison most commonly added to contaminate urine and destroy subsequent enzyme immunoassay procedures used to detect drugs of abuse, on the performance of the Franklin Collector was investigated. 15 c.c. of bleach was added to fresh urine and old urine using the same procedure described above and the subsequent temperatures noted. The results were as follows:

| Experiment #2 | | | |
|---|---|---|---|
| | #1 | #2 | #3 |
| fresh | >104.8 | >104.8 | >104.8 |
| old | <96.0 | <96.0 | <96.0 |

The effect of bleach on urine is to denature proteins normally found in urine, this is an exothermic reaction that generates heat and accounts for the heating of the urine sample beyond the physiologic range such as these results show. However, an old urine sample is sufficiently cool so that even the additional heat generated by this exothermic reaction is insufficient to mimic the temperature of a freshly voided specimen.

In the third and final set of experiments, the effects of the enzyme poison on glucose oxidase were investigated. Glucose oxidase reagent strips, prior to exposure to glucose, appear blue; after exposure to glucose they are brown. Glucose oxidase was dipped in a solution of bleach and urine or urine alone, and then exposed to a glucose solution. The results were as follows:

| Experiment #3 | | | |
|---|---|---|---|
| | #1 | #2 | #3 |
| urine | brown | brown | brown |
| urine + bleach | grey | grey | grey |

This demonstrates that the addition of the appropriate substrate to an enzyme, after the enzyme has been exposed to urine, yields the correct color change only if the urine does not contain an enzyme poison. This serves as an additional check on urine sample integrity by documenting that the sample did not contain an enzyme poison.

The preferred embodiment of the invention 10 may have the thermometer 24 attached to the pedestal 30 by a permanent adhesive so that it may not be removable or tampered. Alternatively, the adhesive may a temporary adhesive so that the thermometer 24 can be moved and read at a subsequent location.

Figure 6:
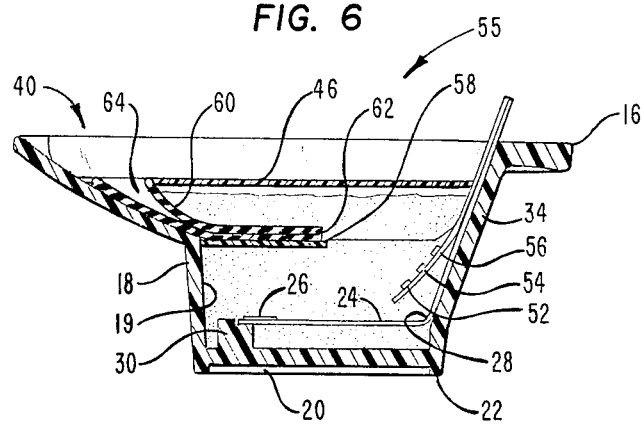
FIG. 6 is an alternative embodiment of the invention in which the one way valve comprises a section of relatively flat, resiliently closed rubber tubing.

An alternative embodiment 55 of the basic invention is shown in FIG. 6. The primary difference between the preferred embodiment 10 and the alternative embodiment 55 is that the trap door 42 has been replaced by a flattened, resilient piece of rubberized tubing 60. Rubberized tubing 60 and trap door 42 both serve the purpose of acting as one way valves 40. Rubberized tubing 60 is located on a flat platform shelf 58. The upper surface 46 prevents urine from entering the base 18 through any route other than through opening 64. The urine sample preferably enters through opening 64 and exits at the opposite end of the tubing 60. A liquid activatable adhesive 62 is located on the interior of the tubing 60 and permanently seals the tubing 60 after it has accepted the urine sample. Alternative embodiment 55 also includes a chemical melting point thermometer 24 and reagent stations 52,54 and 56 similar to those shown in the preferred embodiment 10 of FIGS. 1–5.

Figure 7:
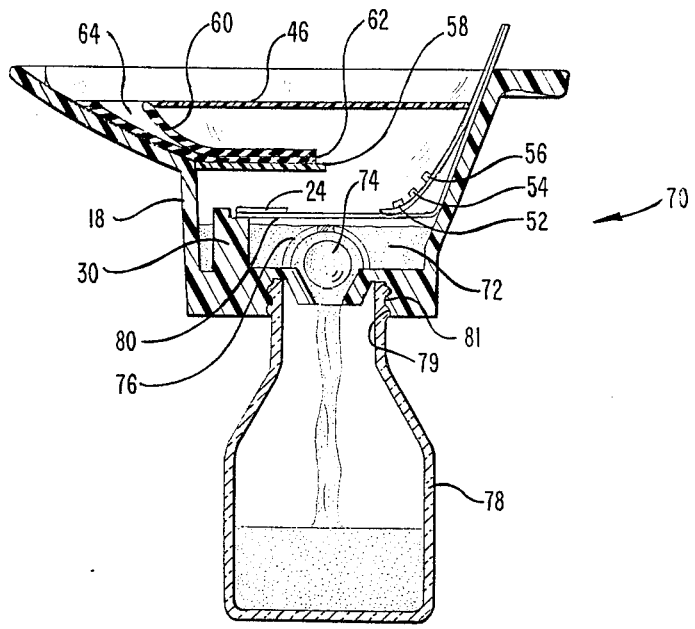
FIG. 7 illustrates another alternative embodiment of the invention in which the one way valve only accepts samples of urine having a specific gravity within a predetermined range.

A specific gravity sensitive embodiment 70 is illustrated in FIG. 7. Embodiment 70 includes a specific gravity sensitive valve 72 which only permits a urine sample to flow into reservoir 78 if the urine sample is within a desired range of specific gravity. Valve 72 includes a float ball 74 captured by a cage 76. A urine collection base 18, similar to that shown in embodiments 10 and 55, is located above reservoir 78. Platform 30 supports a chemical melting point measurement detector 24 and reagent stations 52, 54 and 56 similar to those described in preferred embodiment 10. The purpose of embodiment 70 is only to collect specimens of urine that fall within a predetermined range of specific gravity. It is useful to collect urine in this fashion in order to prevent subjects from watering their urine down thereby diluting the accuracy of the test results. Normal urine has a specific gravity of 1.010–1.040. Accordingly, the ball 74 may have a specific gravity such that it only floats, and therefore accepts into collector 78, urine having a specific gravity of 1.010 or greater. Reservoir 78 includes a threaded top 79 that mates with receiving threads 81 in the bottom of base 18. The threads permit the reservoir to be readily separated from base 18 so that the collected urine may be readily transported to another location for analysis. In this mode the invention 10, 55 or 70 acts as a pass through device to prescreen urine samples for integrity and adulteration prior to more conventional laboratory analysis.

FIGS. 8A and 8B illustrate a urine collection device 90 that is more comfortable for use by males. The only significant difference between the device 90 and the preferred embodiment 10 is the shape of the receptacle 92 which is cylindrical in nature and the incorporation of anti-splatter shield 106 and pour spout 108. The embodiment 90 illustrated in FIG. 8A shows the device prior to receiving a urine sample. The trap door valve 42 is shown in the open state. In FIG. 8B, a sample of urine has been collected in receptacle 92 causing the trap door 42 float to the closed position. Tamper-proof, liquid activatable adhesive 50 seals the trap door 42 shut against the bottom side of upper surface 46. Temperature measuring detector 24 and reagent detector stations 52, 54 and 56 remain the same as in the preferred embodiment 10 of FIGS. 1–5.

Another alternative embodiment 100 is illustrated in FIGS. 9A and 9B. The only difference between embodiments 90 and 100 is that the trap door 42 has been replaced by a piece of resilient, flattened rubber tubing 60 in the same manner that the trap door 42 of embodiment 10 was replaced by a piece of flattened resilient tubing 60 in embodiment 55. Resilient tubing 60 is preferably supported by a shelf like platform 102 so that it describes a generally S-shaped configuration. An upper surface 104 seals off the receptacle 100 so that the urine sample can only be accepted through the opening 64 in tubing 60. Tubing 60 includes a water activatable adhesive 62 similar to that described with reference to FIG. 6. FIG. 9A shows the alternative embodiment prior to the receipt of a urine specimen. FIG. 9B illustrates the embodiment 100 after it has received a urine specimen.

Other variations of the invention are possible given the foregoing description. For example, the one way valves 40 and 60 could be replaced by other tamper proof, one way valves. Similarly, reagents 52, 54 and 56 could be replaced by other reagents. Moreover, while a chemical melting type temperature detector 24 is preferred, other types of temperature detectors are also usable.

While the invention has been described with reference to the preferred embodiment thereof, it will be appreciated by those of ordinary skill in the art that various modifications can be made to the structure and function of the invention without departing from the spirit and the scope of the invention as a whole.

I claim:

1. An integrity preserving and determining urine sample collection apparatus comprising:
   a reservoir having a cavity therein for collecting a sample of urine;
   a tamper-proof one way valve means attached to said reservoir and communicating with the cavity therein for permitting a sample of urine to be collected in said cavity, said one way valve means including means for substantially preventing a first sample of urine collected in said cavity from being removed from said cavity and replaced with a second sample of urine; and,
   a sample freshness detection means including a temperature detecting means for measuring the temperature of a sample of urine as it is being collected and for providing an indication of such a temperature for a prolonged period of time after collection of such a sample thereby serving as an indication that such a sample was fresh when collected,
   wherein said apparatus is substantially tamper proof and said temperature detecting means is located within said cavity which is only accessible to a sample through said one way valve means.

2. The apparatus of claim 1 wherein said temperature detecting means comprises a chemical type of thermometer.

3. The apparatus of claim 1 wherein said preventing means includes:
   adhesive means for sealing said one way valve means after a sample of urine has passed therethrough.

4. The apparatus of claim 1 further comprising:
   anti-splatter shield means attached to said reservoir to prevent urine from splattering.

5. The apparatus of claim 1 wherein said one way valve means further comprises:
   hinge means attached to said reservoir; and,
   trap door means attached to said hinge means for sealing said cavity after it has collected a predetermined volume of urine.

6. The apparatus of claim 5 wherein said trap door has a specific gravity less than a typical urine sample so that said trap door closes as said cavity fills with urine.

7. The apparatus of claim 1 further comprising:
sample adulteration detection means located in said cavity for detecting if a sample collected in said cavity has been adulterated.

8. The apparatus of claim 7 wherein said sample adulteration detection means includes:
pH detection means located in said cavity for detecting the pH of a sample collected in said cavity.

9. The apparatus of claim 7 wherein said sample adulteration detection means includes:
a specific gravity detection means located in said cavity for determining the specific gravity of a sample collected in said cavity.

10. The apparatus of claim 7 wherein said sample adulteration detection means includes:
enzyme poison detecting means located in said cavity for detecting if adulterants have been added to a sample collected in said cavity to neutralize enzymes therein.

11. The apparatus of claim 10 wherein said enzyme poison detection means comprises glucose oxidase.

* * * * *